US008192537B2

(12) United States Patent
Alemao

(10) Patent No.: US 8,192,537 B2
(45) Date of Patent: Jun. 5, 2012

(54) METHOD AND APPARATUS FOR ODOR CONTROL USING PANELS OF ACTIVATED CARBON CLOTH

(76) Inventor: Thaddeus Alemao, Oceanside, NY (US)

(*) Notice: Subject to any disclaimer, the term of this patent is extended or adjusted under 35 U.S.C. 154(b) by 0 days.

(21) Appl. No.: 11/287,721

(22) Filed: Nov. 28, 2005

(65) Prior Publication Data
US 2006/0156926 A1 Jul. 20, 2006

(51) Int. Cl.
*B01D 53/02* (2006.01)

(52) U.S. Cl. .......... 96/108; 96/134; 126/383.1

(58) Field of Classification Search .......... 95/107; 96/134, 117.5, 108; 422/292; 55/385.1; 206/278; 126/383.1, 384
See application file for complete search history.

(56) References Cited

U.S. PATENT DOCUMENTS

| | | | | | |
|---|---|---|---|---|---|
| 1,622,351 | A * | 3/1927 | Salmon | .................. | 126/383.1 |
| 1,942,900 | A * | 1/1934 | Peters | .................. | 96/148 |
| 2,524,554 | A * | 10/1950 | White | .................. | 96/148 |
| 2,587,773 | A * | 3/1952 | Sell et al. | .................. | 96/148 |
| 2,999,559 | A * | 9/1961 | Boyer | .................. | 126/383.1 |
| 3,343,345 | A * | 9/1967 | Carolan | .................. | 55/511 |
| 3,822,698 | A * | 7/1974 | Guy | .................. | 128/201.25 |
| 4,415,342 | A * | 11/1983 | Foss | .................. | 95/107 |
| 4,944,884 | A * | 7/1990 | Naoi | .................. | 210/692 |
| 5,458,772 | A * | 10/1995 | Eskes et al. | .................. | 210/238 |
| 5,494,500 | A * | 2/1996 | Ikenaga et al. | .................. | 96/109 |
| 5,584,234 | A | 12/1996 | Baillieul et al. | .................. | 99/403 |
| 5,690,922 | A * | 11/1997 | Mouri et al. | .................. | 424/76.1 |
| 5,772,738 | A * | 6/1998 | Muraoka | .................. | 96/129 |
| 5,814,396 | A | 9/1998 | Weidner et al. | .................. | 428/213 |
| 5,912,423 | A | 6/1999 | Doughty et al. | .................. | 95/107 |
| 6,029,652 | A * | 2/2000 | Riedl | .................. | 126/299 C |
| 6,056,146 | A * | 5/2000 | Varakian et al. | .................. | 220/370 |
| 6,346,143 | B1 | 2/2002 | McGowan | .................. | 96/117.5 |
| 6,364,936 | B1 | 4/2002 | Rood et al. | .................. | 95/115 |
| 6,412,628 | B1 | 7/2002 | Tramposch | .................. | 206/207 |
| 6,430,031 | B1 * | 8/2002 | Dispennette et al. | .................. | 361/502 |
| 6,497,738 | B2 * | 12/2002 | Lin | .................. | 55/385.1 |
| 6,565,627 | B1 * | 5/2003 | Golden et al. | .................. | 95/96 |
| 6,997,975 | B2 * | 2/2006 | Stefanoni | .................. | 96/117.5 |
| 2002/0129711 | A1 * | 9/2002 | Oda et al. | .................. | 96/134 |
| 2002/0185013 | A1 | 12/2002 | London | .................. | 99/450 |
| 2003/0010767 | A1 | 1/2003 | Li | .................. | 219/417 |
| 2003/0049187 | A1 * | 3/2003 | Kaiser | .................. | 422/292 |
| 2003/0170200 | A1 | 9/2003 | Ichinose et al. | .................. | 424/76.1 |
| 2004/0055079 | A1 * | 3/2004 | Haaga | .................. | 2/455 |
| 2004/0069154 | A1 * | 4/2004 | Stefanoni | .................. | 99/408 |
| 2004/0173099 | A1 * | 9/2004 | Ruckert et al. | .................. | 96/108 |
| 2004/0187702 | A1 * | 9/2004 | Xu | .................. | 99/422 |
| 2005/0172813 | A1 * | 8/2005 | Mifune et al. | .................. | 96/108 |

(Continued)

OTHER PUBLICATIONS

Cuisipro, http://web.archive.org/web/20031013223817/http://www.cooking.com/products/shprodde.asp?SKU=110319, Stainless Steel Splatter Guard with Feet, Oct. 20, 2003, Cooking.com.*

(Continued)

*Primary Examiner* — Duane Smith
*Assistant Examiner* — Amber Orlando
(74) *Attorney, Agent, or Firm* — Alfred M. Walker; John F. Vodopia; Lee Grossktenz Hechtel

(57) ABSTRACT

A method of containing and reducing unwanted odors and fumes and removing those fumes from the immediate surroundings of the apparatus.

14 Claims, 4 Drawing Sheets

U.S. PATENT DOCUMENTS

2007/0151877 A1* 7/2007 Newman .................. 206/278
2009/0142224 A1* 6/2009 Urlaub et al. .................. 422/5

OTHER PUBLICATIONS

"Activated Charcoal Cloth for the Electric Desorbtion of Organic Molecules", Charcoal Cloth International, Tyne & Wear, England, U.K., 5 pg. Brochure "Carbosorb Plus Face Mask," Charcoal Int'l, Tyne & Wear, U.K., 1 pg.

"Challenge Carbon Technology—Advanced Activated Carbon Fiber Fabrics For NBC Protective Technology", Challenge Carbon Technology Co., Ltd., 3 pg. Website, Jan. 2005.

Kloeppel; James E., "Vapor-recovery system captures and recycles air pollutants", Univ. of IL @ Urbana-Champaign, 2004, 2 pg. News article.

Millan; Leslie, "VaPRRS™ Technology", Office of Tech. Mgmt, Univ. of IL @ Urbana-Champaign, 2004, 10 pgs.

"Splatter Screen 13 inch Plastic Handle", Dorothy McNett's Place, 2004 1 pg. Website adv.

"Splatter Screens & Frying Tools", the gadgetsource.com, 2004, 1 pg. website adv.

Zorflex® Pure—Chemviron Carbon, Calgon Carbon Corp., Pittsburgh, PA, 2000, 15 pgs.

Kunwar P. Singh, et al, Vapor-Phase Adsorption of Hexane and Benzene on Activated Carbon Fabric Cloth: Equilibria and Rate Studies, Apr. 10, 2002, one page,. I&EC Research, Ind.Eng.Chem.Res., 41 (10), published in U.S.

* cited by examiner

METHOD AND APPARATUS FOR ODOR CONTROL USING PANELS OF ACTIVATED CARBON CLOTH

FIELD OF THE INVENTION

The present disclosure relates to odor capture and control devices.

BACKGROUND OF THE INVENTION

Activated carbon cloth (ACC) is an alternative to traditional activated carbon granules for many filtering and odor reducing applications. activated carbon cloth (ACC) is available as a single weave, double weave, or knitted jersey fabric that is totally constructed of activated carbon fibers. It can also be supplied laminated to other fabric for low temperature applications such as military garments. For many applications, activated carbon cloth (ACC) has up to 250% of adsorption capacity of activated carbon granules with enhanced mass and heat transfer qualities.

The prior art reveals several applications of activated carbon granules to odor control or vapor capture. Activated carbon cloth (ACC) is applied to the capture and recovery of volatile organic compounds (VOC's) in U.S. Pat. No. 6,364,936 of Rood et al. The electrical conductivity aspect of activated carbon cloth (ACC) is used to heat the activated carbon cloth (ACC) filters electrically to boil off the adsorbed VOC's during the recovery phase.

U.S. Pat. No. 5,912,423 of Doughty et al discloses a method of purifying an air stream in a building or vehicle by passing the air stream through an adsorbent activated carbon cloth, and then regenerating the carbon cloth by electrically heating the carbon cloth for desorbing the captured contaminants and venting them away from the carbon cloth by a purging air stream, enabling the carbon cloth to be reused.

U.S. Pat. No. 6,346,143 of McGowan relates to an adsorptive filter for refrigerators and freezers; a woven or nonwoven filter matrix with granules or powder elements of activated carbon and/or other compounds combined in to the matrix, is used as the odor-reducing element.

U.S. Pat. No. 5,584,234 of Baillieul et al. adds a vapor-condensing trap to a household type deep fryer to condense the vapors given off by the food preventing their odorous entry into the air.

Patent Publication No. US 2003/0010767 of Li describes a multifunctional cooking system consisting of a stand-alone electrically heated cooker with an "odor eliminating filter assembly 15" in the lid as shown in FIG. 1. No further description of the filter is revealed.

Patent Publication No. US 2004/0187702 of Xu relates to a forced venting fry utensil that includes "a disposable activated charcoal filter 42b" in the exhaust venting conduit. This invention forces air into the fry utensil, which is then vented through the venting conduit for reducing cooking odors.

None of the prior art cited uses of activated carbon cloth (ACC) panels to reduce odor from domestic frying pans, commercial frying bins, gym bags, hats or kitchen garbage cans.

OBJECTS OF THE INVENTION

It is therefore an object of the present disclosure to provide an odor control using panels of activated carbon cloth.

It is also an object of the present disclosure to provide an odor and splatter control for frying pans.

Other objects which become apparent from the following description of the present disclosure.

SUMMARY OF THE INVENTION

The first method of odor reduction of this disclosure uses an activated carbon cloth (ACC) panel incorporated into a splatter screen used atop a fry pan. The activated carbon cloth is comprised of activated carbon fibers which are woven or knitted as part of a synthetic material. Incorporating an activated carbon cloth into a splatter screen is greatly advantageous over the prior art, because the heat generated while cooking and utilizing the carbon cloth splatter screen acts to both regenerate the carbon particles and simultaneously allow the carbon cloth to efficiently adsorb any water vapors and odorous fried particles released during the cooking process. The cooking vapors and fumes that are emitting from the food stuff are retained with the activated carbon cloth (ACC) and the vapors are prevented from dissipating into the surroundings during cooking. The cooking also results in desorbing of the accumulated odorous particles and reduces splatter of frying particles.

Many food items, such as onions or peppers, produce strong odors while being fried. Besides the odors being a nuisance, they can be even more objectionable to a person undergoing chemotherapy or having other afflictions (such as flu) causing nausea. With household members working different shifts, or sleeping different hours, the wafting of cooking odors into the bedroom often acts as an "alarm clock" to waken a sleeping person.

It has been found that a layer of activated carbon cloth (ACC) incorporated into a splatter screen is very effective at greatly reducing the odors emitted into the ambient air in the vicinity. The large surface area of the activated carbon fibers knitted or woven in the cloth enables the carbon particles to adsorb cooking odors from cooking vapors and the like. Generally, organic vapors exhibit increasing adsorption with increasing concentration during the physical adsorption process. A non-laminated activated carbon cloth (ACC) fabric is more efficient and practical when used since the continuous heat and flame proximity evaporates and wastes the lamination of a typically laminated version or type. The lamination will evaporate, eventually rendering a non-laminated cloth, but it wastes heat and energy until the lamination is evaporated.

The activated carbon cloth can be manufactured from either woven or knitted rayon materials. Typically the carbon cloth is less than 1 mm in thickness, preferably from 0.4 to 0.6 mm in thickness, although the a slightly thicker or thinner material is acceptable, such as being between 0.2 mm and 3.0 mm in thickness. It is made of a matrix of intertwined carbon filaments, forming a conductive matrix conducive to adsorption of airborne odorous particles.

Three embodiments of the splatter screen are defined. In the first embodiment, a metal or high temperature, heat resistant plastic frame with attached handle is used to mechanically support the activated carbon cloth (ACC) fabric at its edge; this is used as the only layer of the splatter screen. In the second embodiment, a wire screen layer (or a molded integral plastic perforated panel) is used as the lower layer below the activated carbon cloth (ACC) layer and above the frying food in a skillet, pot, deep fryer or the like. In the third embodiment, the activated carbon cloth (ACC) layer is sandwiched or layered between two wire mesh screen and/or perforated plastic layers. In this embodiment, the splatter screen includes a layer of activated carbon cloth layered between at least one mesh screen layer and a second material, typically a second mesh screen. The mesh screen layers are held together by fasteners or by a crimping material that crimps the edges of all the layers together to maintain a permanent form. The crimping material is heat resistant in this embodiment and may be varied for other embodiments.

When cooking and heating is not involved, the material which forms the second layer may be varied to include cotton, canvas, wool, synthetic fibers, combinations and the like, where the article is designed for uses other than cooking.

The splatter screen may be subsequently washed in soap and water to clean it after use. While some of the water will air dry near the activated carbon cloth (ACC) outer surfaces after washing, the heat of cooking will boil off any adsorbed water vapor and other odorous particles, to rejuvenate the activated carbon cloth (ACC) layer.

The adsorbed molecules are released from the surface of the carbon particles by the heat of the frying process, and optionally by a subsequent washing process because they were initially held by the Van der Waals forces of physical/electrical attraction.

This release of the adsorbed particles from the carbon particle surface allows to carbon particles to again adsorb molecules, which are filtered or passed through the carbon particles. This release process is referred to as regeneration of activated carbon.

Additionally, besides being used in frying pan skillet uses as noted above, the activated carbon cloth (ACC) fabric can also be put in a cover cap frame for a commercial deep fryer screened container bin for frying food products, such as French fried potatoes, fried shrimp, etc. The activated carbon cloth (ACC) cover cap can be attached by hinges to the screened food container bin being dipped into the frying oil or other frying medium.

The second method of odor reduction of this invention involves the use of one or two rectangular panels of laminated activated carbon cloth (ACC) removably attached to the inner side or sides of a gym bag. The laminated activated carbon cloth (ACC) panel is also attached to a semi-rigid springy plastic screen frame. Shallow holding pouches are sewn into the sides of the gym bag to activated carbon cloth accept the narrow ends of the activated carbon cloth (ACC) panels. Alternatively, the activated carbon cloth (ACC) can be fastened in place with reusable fasteners, such as VELCRO® hook and loop fasteners.

These panels can be washed periodically to remove the adsorbed odorous vapors. Since they are laminated to an absorbent fabric, these activated carbon cloth (ACC) panels do not require heat to be rejuvenated after washing; they will effectively air dry.

The third method of odor reduction of this invention involves the introduction of activated carbon cloth (ACC) panels into the interior of hats, which are not washable in water. Men's or women's straw or felt hats, or leather hats fall into this category.

Two embodiments of hat panels are described. The first embodiment is a long narrow laminated activated carbon cloth (ACC) strip attached to a thin plastic screen. In another embodiment, the ACC may also be non-laminated. It should be biased to spring into a large loop with a gap at the ends. This is simply fitted inside a felt type hat (tall shape) on the inside of the sweat band. The strip of this embodiment is wider than the sweat band, but should fit easily inside a hat. The second embodiment of hat panel is for low hat designs such as leather short brim hats. While there would be no room for a strip as the first embodiment, a wide strip with rounded ends can be fitted inside the hat against the top inner surface. It would be held in the side crease; it can be trimmed to fit. The construction of this embodiment is the same as that of the first hat embodiment. In a similar fashion, a strip of activated carbon cloth (ACC) may be inserted into collars of shirts, coats, jackets and the like, wrist bands of shirts or coats, jackets and the like, and other clothing that would benefit from the use of ACC to prevent or reduce odor.

The fourth method of odor reduction of this invention is to introduce a panel of laminated activated carbon cloth (ACC) into the inside surface of the lid of a kitchen garbage can. A large rectangular or round activated carbon cloth (ACC) panel attached to a plastic or metal screen is removably attached to the underside of the garbage can lid with spring clips, which are provided. As in all the laminated activated carbon cloth (ACC) applications, this panel can be washed in detergent and rinsed. It can then just be air dried.

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

Figure 1:
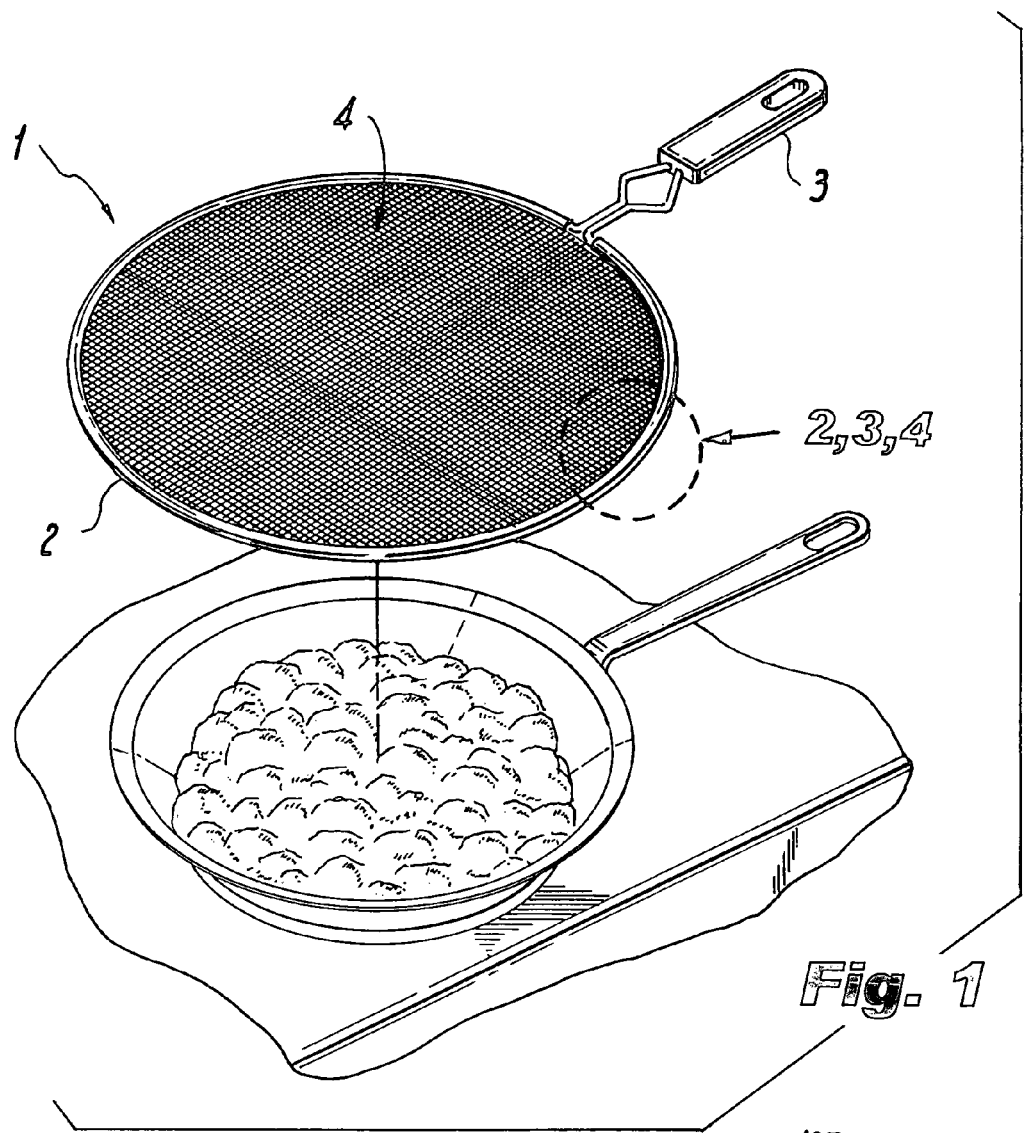
FIG. 1 is a Top Perspective view of odor reducing splatter screen of this invention, for a stove-top skillet frying pan.

An odor reducing splatter screen 1 is shown in FIG. 1. Odor reducing splatter screen 1 has round frame 2, handle 3 and screen area 4. Three different embodiments according the configuration of screen area 4 are presented.

Figure 1A:
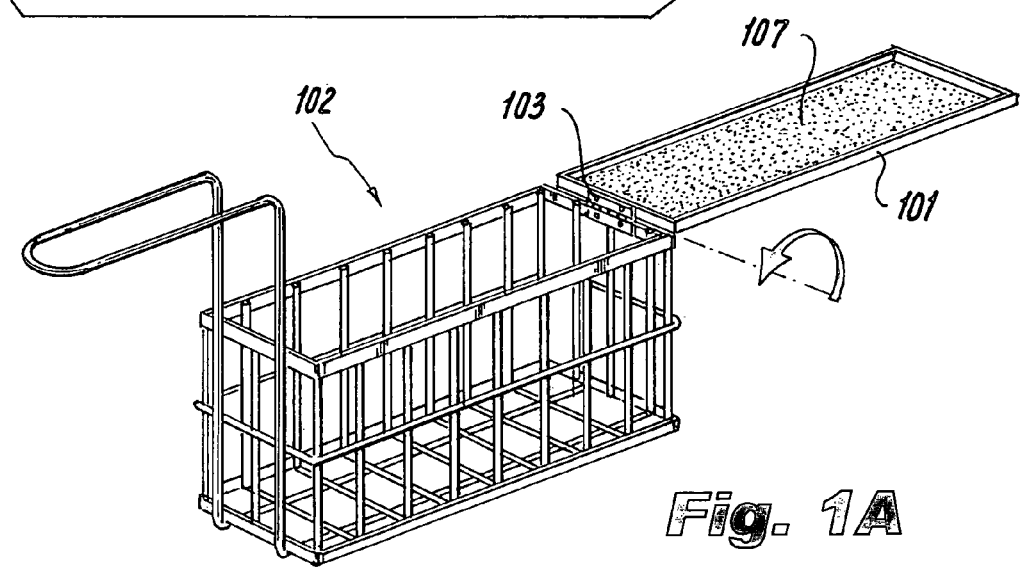
FIG. 1A is a perspective view of another embodiment for an odor reducing splatter screen of this invention, for a commercial fryer bin.

In addition to being used in a frying pan skillet as in FIG. 1, FIG. 1A shows that the activated carbon cloth (ACC) fabric 107 can also be put in a cover cap frame 101 for a commercial deep fryer screened container bin 102 for frying food products, such as French fried potatoes, fried shrimp, etc. The activated carbon cloth (ACC) cover cap frame 101 can be attached by one or more hinges 103 to the screened food container bin 102 being dipped into the frying oil or other frying medium.

Figure 2:
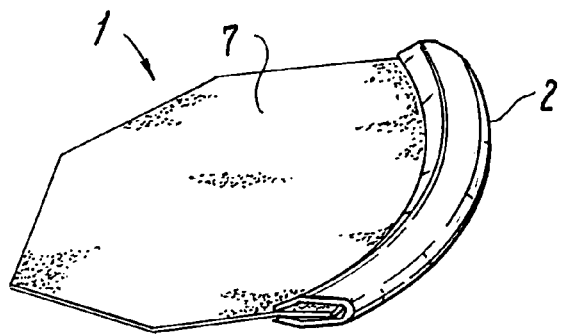
FIG. 2 is a local perspective view of a one embodiment of a splatter screen, taken at arrow 2 of FIG. 1.

In FIG. 2, a perspective view of a single layer of activated carbon cloth (ACC) 7 is shown being supported by frame 2.

Figure 3:
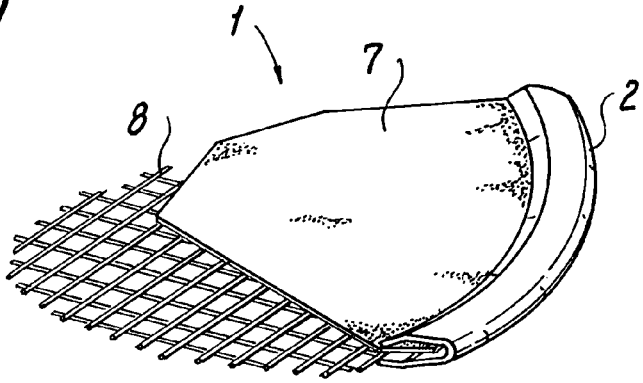
FIG. 3 is a local perspective cutaway view of another embodiment of a splatter screen, taken at arrow 3 of FIG. 1.

In FIG. 3, a lower screen 8 is introduced between the food being fried and activated carbon cloth (ACC) panel 7. This protects activated carbon cloth (ACC) layer 7 from some of the grease splatter.

Figure 4:
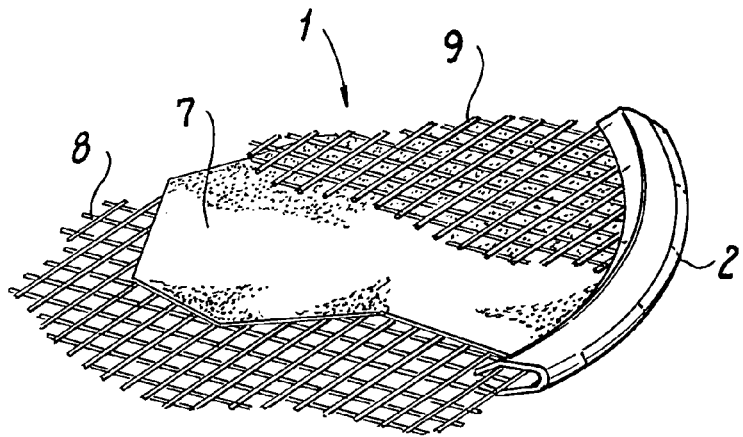
FIG. 4 is a local perspective cutaway view of a further embodiment of a splatter screen, taken at arrow 4 of FIG. 1.

In FIG. 4, two screens are shown. Screen 8 as in FIG. 3 is now joined by screen 9 on top of activated carbon cloth (ACC) layer 7. This gives mechanical protection to activated carbon cloth (ACC) layer 7 from both sides. Note that activated carbon cloth (ACC) layer 7 is not laminated to another fabric as in the other applications and embodiments to be described which are all room temperature (or below) applications. Screen layers can be perforated molded high temperature plastic or metal such as aluminum or stainless steel.

Figure 5:
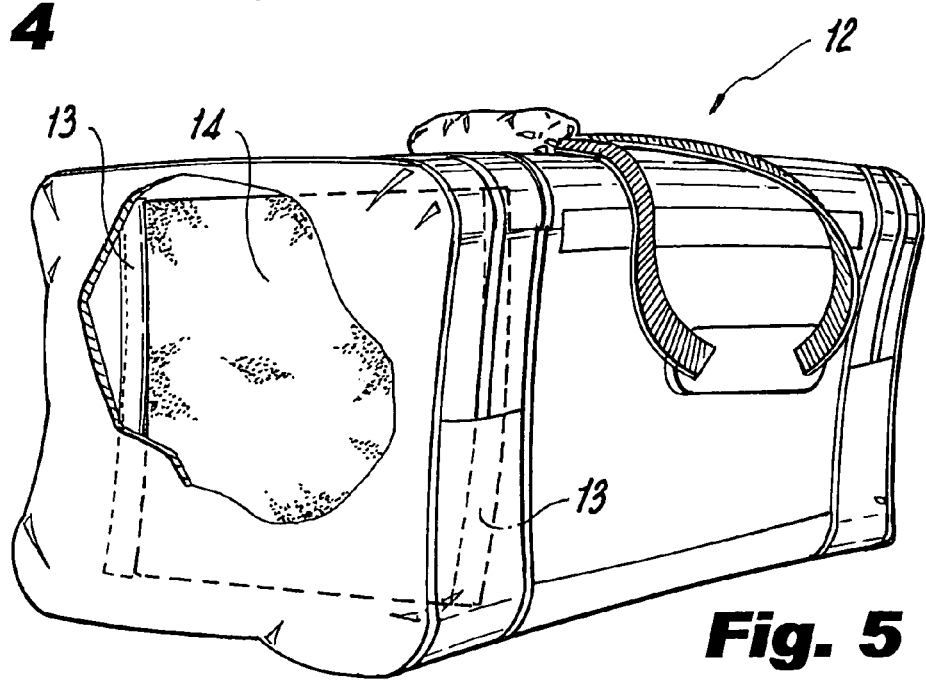
FIG. 5 is a Perspective view of an odor reducing gym bag of this invention with an interior aperture showing an activated carbon cloth (ACC) panel within.

FIG. 5 shows a view of odor reducing gym bag 12 with laminated activated carbon cloth (ACC) panel 14 held in shallow stitched pockets 13 at each end. Note that panel 14 is integral with a springy screen which permits it to be inserted and withdrawn from pockets 13 at will. A single panel on one side can be used, but more effectiveness is afforded by using one panel 14 on each side of gym bag 12. Alternatively, removable fasteners, such as VELCRO® hook and loop fasteners can be used.

Figure 6:
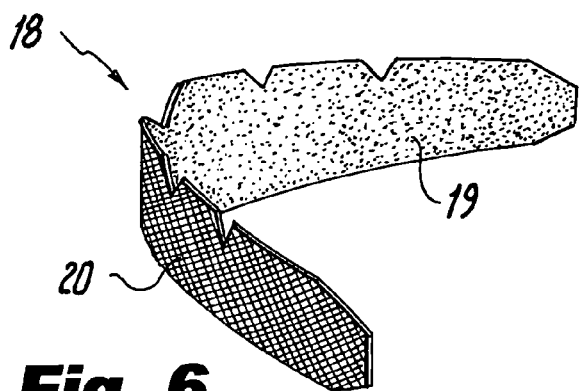
FIG. 6 is a Perspective view of a hat odor reducing band of this invention.

FIG. 6 shows a springy laminated activated carbon cloth (ACC) panel 18 with outer screen surface 20 and inner fabric surface 19.

Figure 7:
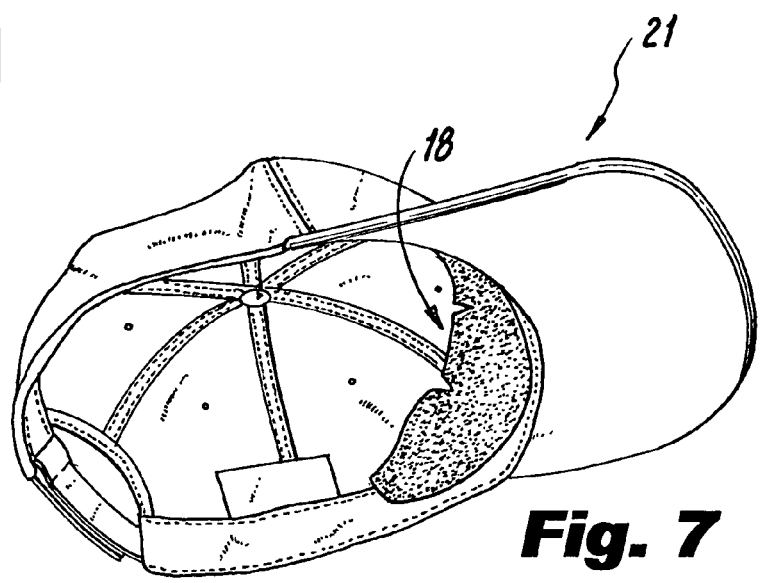
FIG. 7 is a Perspective view of a hat with a panel of an activated carbon cloth (ACC) installed therein.

As best seen in the underside perspective view of cap 21 in FIG. 7, panel 18 may be adhered, stitched or otherwise affixed to the sweat band of cap 21.

Figure 8:
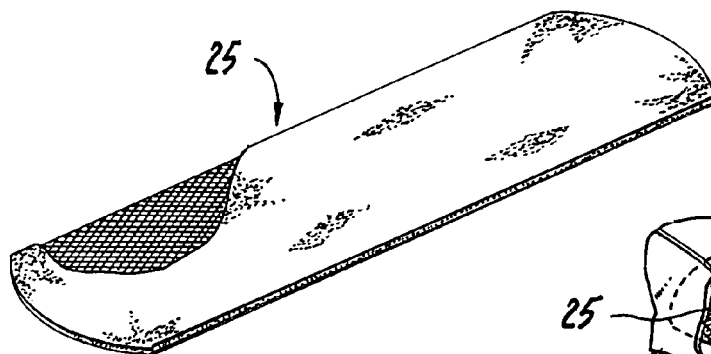
FIG. 8 is a Perspective view in partial cutaway, of another hat odor reducing panel of this invention.

FIG. 8 illustrates an alternated-shaped embodiment of a laminated activated carbon cloth (ACC) panel 25, containing a springy screen layer as shown in partial cutaway.

Figure 9:
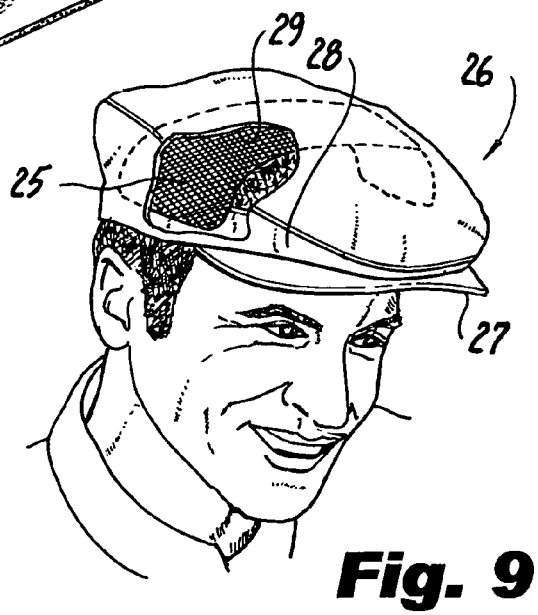
FIG. 9 is a Top perspective view of a short brim hat with an activated carbon cloth (ACC) panel of second embodiment installed on interior surface of hat.

FIG. 9 is a perspective view of a short brimmed cap 26, which is typically leather or wool. This leisure-type cap has a short front brim 27, folded back side 28 and an underside surface 29. Note that panel 25 spans the underside surface 29 of cap 26, and may be removably inserted into the sweat band as shown, or otherwise permanently affixed to the interior surface of cap 26.

Figure 10:
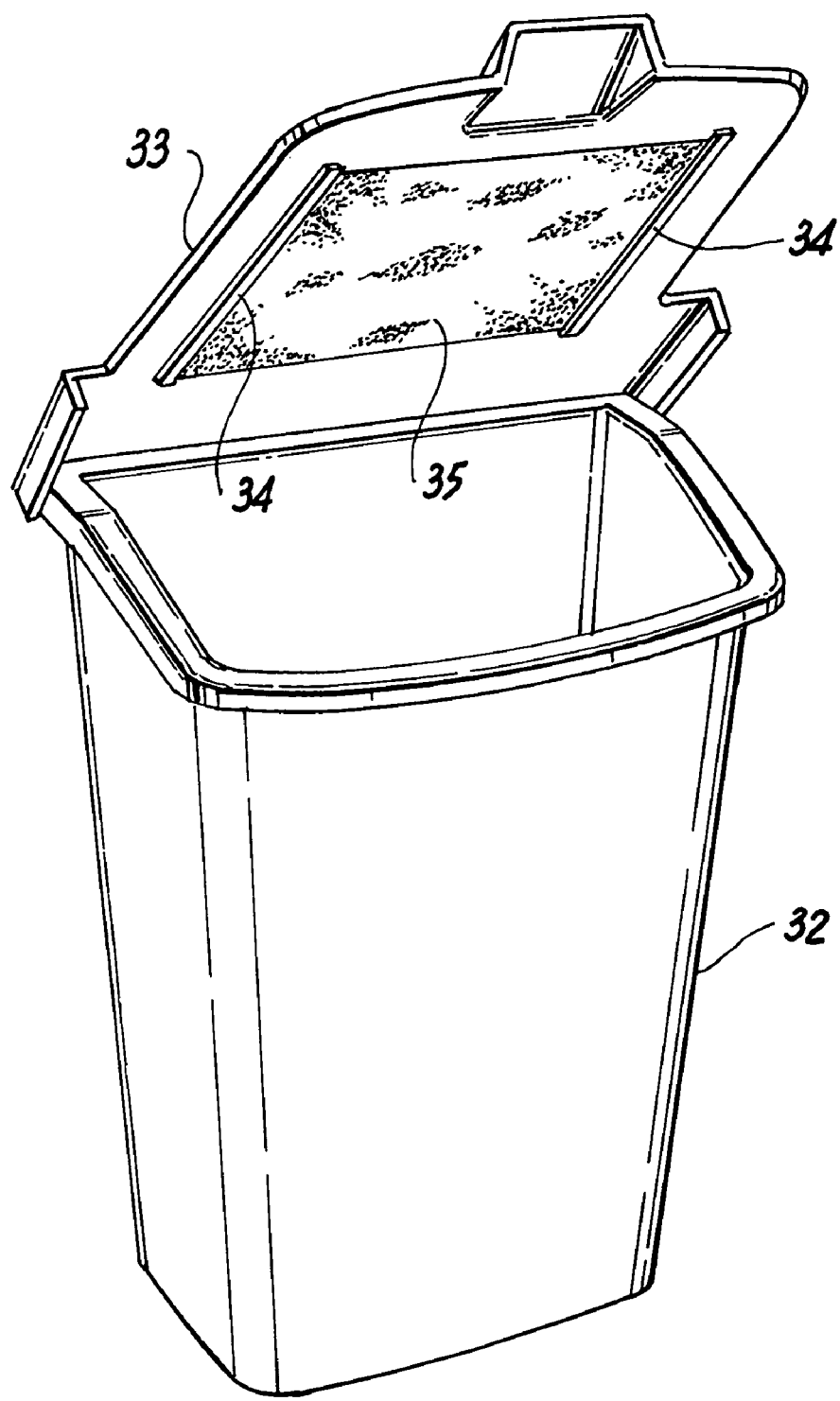
FIG. 10 is a Perspective view of a kitchen garbage can with an odor reducing activated carbon cloth (ACC) panel installed on inner surface of lid.

FIG. 10 shows kitchen garbage can 32 with hinged lid 33. Rectangular activated carbon cloth (ACC) panel 35 is held to the underside of lid 33 via spring clips 34. Note that for a round garbage can with round lid, laminated activated carbon cloth (ACC) panel 35 would be round. Panel 35 is constructed of a layer of laminated activated carbon cloth (ACC) fabric attached to a screen layer. Panel 35 can be removed for washing.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention.

What is claimed is:

1. An odor reducing apparatus for retaining emitted cooking vapors and reducing vapors from dissipating into the surroundings during cooking comprising:
    a removable heat resistant circular loop frame adapted to fully enclose an open top of a stove top pan under cooking conditions,
    a substrate of activated carbon cloth comprising a matrix of intertwined carbon filaments that is permanently attached to said heat resistant circular loop frame and extending over a whole area encompassed by said loop frame,
    heat resistant open mesh screening in said frame positioned on one side of said activated carbon cloth for protecting said substrate from cooking spatter emanating from said frying pan, whereby all of the one side of said substrate is protected against said cooking spatter, and
    a heat resistant handle,
    wherein said loop frame and said substrate of activated carbon cloth are adapted to cover said pan during use,
    wherein said activated carbon cloth captures particles in an upward moving gaseous plume comprising the cooking vapors that passes through said of activated carbon cloth, which is washable after use to remove said cooking splatter and particles, and
    wherein said heat resistant open mesh screening both supports said substrate of activated carbon cloth and functions as a spatter screen for said pan.

2. The odor reducing apparatus for retaining emitted cooking vapors and reducing vapors from dissipating into the surroundings during cooking as in claim 1 further comprising a second heat resistant mesh screening on an opposite side of said activated carbon cloth with said substrate of activated carbon cloth therebetween to provide mechanical protection for said activated carbon cloth.

3. The odor reducing apparatus as in claim 1 wherein said activated carbon cloth comprises a single layer.

4. The odor reducing apparatus as in claim 1 wherein said activated carbon cloth is between 0.2 mm and 3.0 mm in thickness.

5. The odor reducing apparatus as in claim 3 wherein said activated carbon cloth is between 0.4 mm and 0.6 mm in thickness.

6. A method of retaining emitted cooking vapors and reducing vapors from dissipating into the surroundings during cooking comprising:
    a) providing an odor reducing apparatus, the apparatus comprising a heat resistant loop frame supporting an open mesh splatter screen extending over a whole area encompassed by said loop frame, a heat resistant handle and a substrate of woven activated carbon cloth permanently attached to said loop frame and extending over the whole area encompassed by said loop frame on one side of said screen;
    b) covering completely a stove-heated open top cooking pan with said odor reducing apparatus such that said screen on said one side of said substrate facing said open top cooking pan during cooking use removes cooking particles from gaseous convection comprising the cooking particles and rising from said open top cooking pan in an upwardly flowing plume and said open mesh splatter screen prevents splatter from escaping from said cooking pan thereby containing odors within the activated carbon cloth of the apparatus, and
    c) after cooking use, washing said splatter screen and said woven activated carbon cloth in soap and water in preparation for reuse by said apparatus.

7. A method of retaining emitted cooking vapors and reducing vapors from dissipating into the surroundings during cooking of claim 6 wherein, the activated carbon cloth comprises a single layer.

8. A method of retaining emitted cooking vapors and reducing vapors from dissipating into the surroundings during cooking of claim 6 wherein, the activated carbon cloth is in a range of 0.2 mm to 3.0 mm thickness.

9. A method of reducing unwanted odors of claim 6, wherein the activated carbon cloth comprises a single layer.

10. A splatter screen in combination with a stove top cooking utensil for simultaneously retaining emitted cooking odors and limiting splattering comprising:
   a frame having an opening large enough and enclosing an open top of said cooking utensil;
   a single layer activated carbon cloth of woven construction that is permanently attached to said frame and fully covers said opening;
   a heat resistant open mesh in said frame positioned for protecting said substrate from cooking splatter; and
   a handle attached to said frame whereby a user can place said frame with said open mesh and said activated carbon cloth over the open top of said cooking utensil while cooking to adsorb cooking odors and at the same time preventing splattering on said stove top,
   wherein upon heating said stove top cooking utensil, a convection is generated forming an upward flowing plume within which cooking odor particles are contained, which cooking particles are adsorbed by the activated carbon cloth as the upward flowing plume passes therethrough, and any cooking splatter caused by said heating is captured by said open mesh, and
   wherein said frame with said open mesh and said activated carbon cloth is washable after use to remove said particles and said cooking splatter.

11. The splatter screen of claim 10 in which said carbon cloth has a thickness in the range of 0.2 to 3.0 mm.

12. The splatter screen of claim 10 in which said mesh is a wire screen layer mounted in said frame as a lower layer under said carbon cloth for providing support for said carbon cloth.

13. The splatter screen of claim 10 in which said carbon cloth is sandwiched between upper and lower layers of wire mesh screens or perforated plastic.

14. A method of preventing splatter and simultaneously retaining emitted cooking odors from an open top of a cooking utensil on a stove top comprising the steps of:
   while applying heat to the cooking utensil, using a handle attached to a splatter shield comprising a frame, an underlying heat resistant open mesh screen and a single layer, woven activated carbon cloth that is permanently attached to said frame to fully cover said open top such that cooking odor particles and water vapor contained in an upwardly rising plume from said cooking utensil passes through the carbon cloth and are efficiently adsorbed while the underlying heat resistant mesh screen protects the activated carbon cloth from cooking splatter; and
   cleaning said splatter shield using soap and water and drying after use.

\* \* \* \* \*